United States Patent [19]

Lieb et al.

[11] 4,318,695
[45] Mar. 9, 1982

[54] HANDPIECE

[75] Inventors: Nathaniel H. Lieb, Narberth; Albert D. Alderman, Jr., Skippack, both of Pa.

[73] Assignee: Venture Technology, Inc., Conshohocken, Pa.

[21] Appl. No.: 144,107

[22] Filed: Apr. 28, 1980

[51] Int. Cl.³ .............................................. A61C 1/05
[52] U.S. Cl. .................................. 433/132; 433/133; 433/82
[58] Field of Search ............... 433/129, 132, 126, 127, 433/82

[56] References Cited

U.S. PATENT DOCUMENTS

| 2,945,299 | 7/1960 | Fritz | 433/132 |
|---|---|---|---|
| 3,120,706 | 2/1964 | Turchi et al. | 433/129 |
| 3,175,293 | 3/1965 | Borden | 433/82 |
| 3,199,196 | 8/1965 | Lieb et al. | 433/129 |
| 3,499,223 | 3/1970 | Lieb et al. | 433/129 |
| 3,624,905 | 2/1970 | Barsby | 433/82 |
| 3,962,788 | 6/1976 | Flatland | 433/129 |
| 4,015,489 | 4/1977 | Lieb et al. | 433/129 |

Primary Examiner—Robert Peshock
Attorney, Agent, or Firm—Caesar, Rivise, Bernstein & Cohen, Ltd.

[57] ABSTRACT

An air driven dental handpiece having an air turbine at one end thereof. Collet means for securing a dental bur therein are positioned within the air turbine. The air turbine is mounted in ball bearings, which are in turn resiliently mounted within the turbine housing. The handpiece handle is hollow and includes air and water tubes therein. The air and water are mixed within the handpiece at the point of expulsion from the handpiece, thereby creating a coolant mist or fog on the dental bur and the tooth being drilled.

11 Claims, 9 Drawing Figures

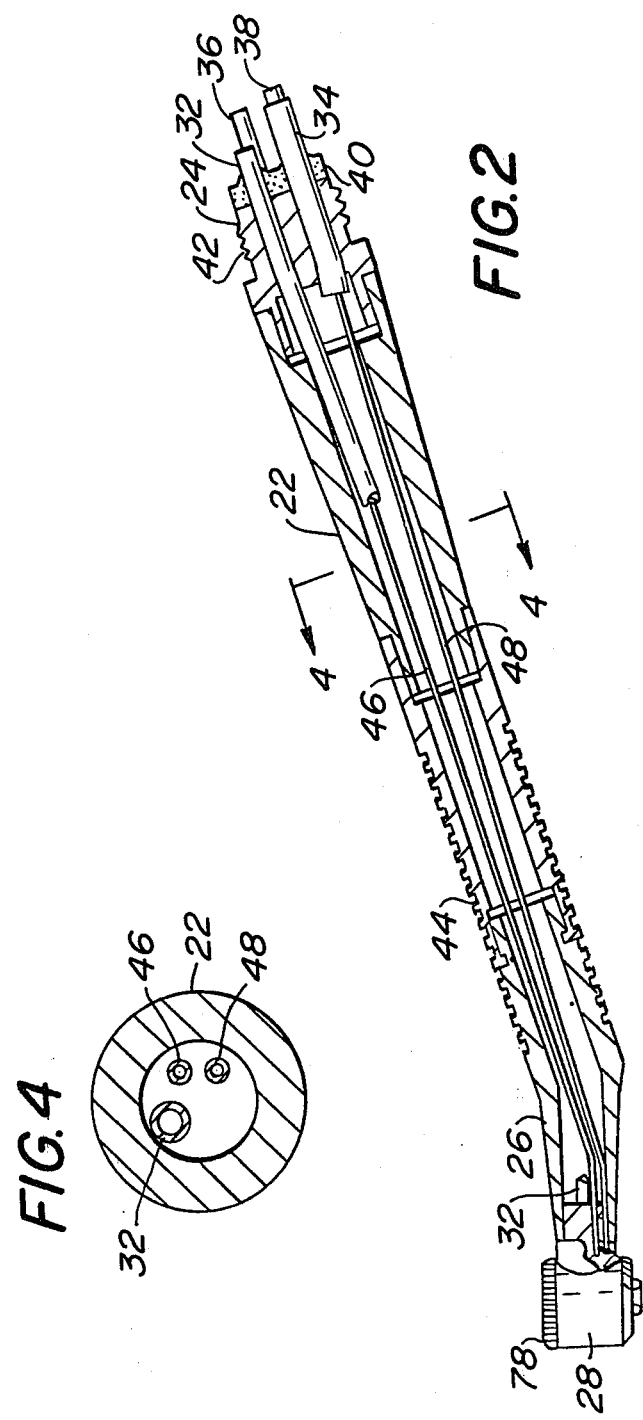

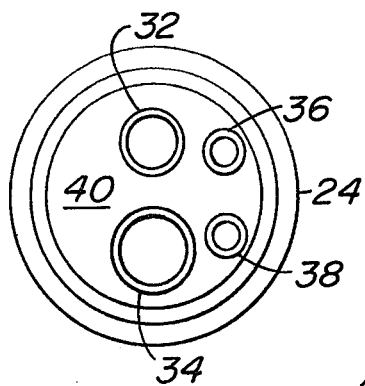
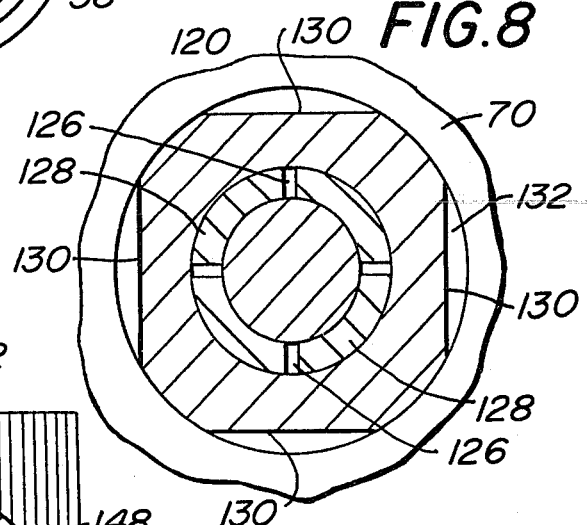
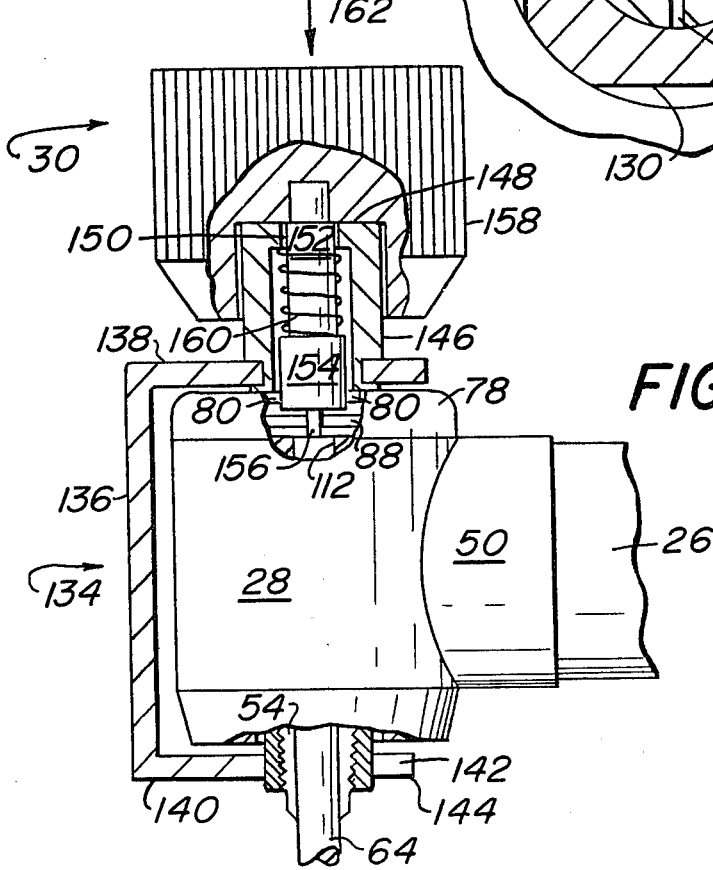

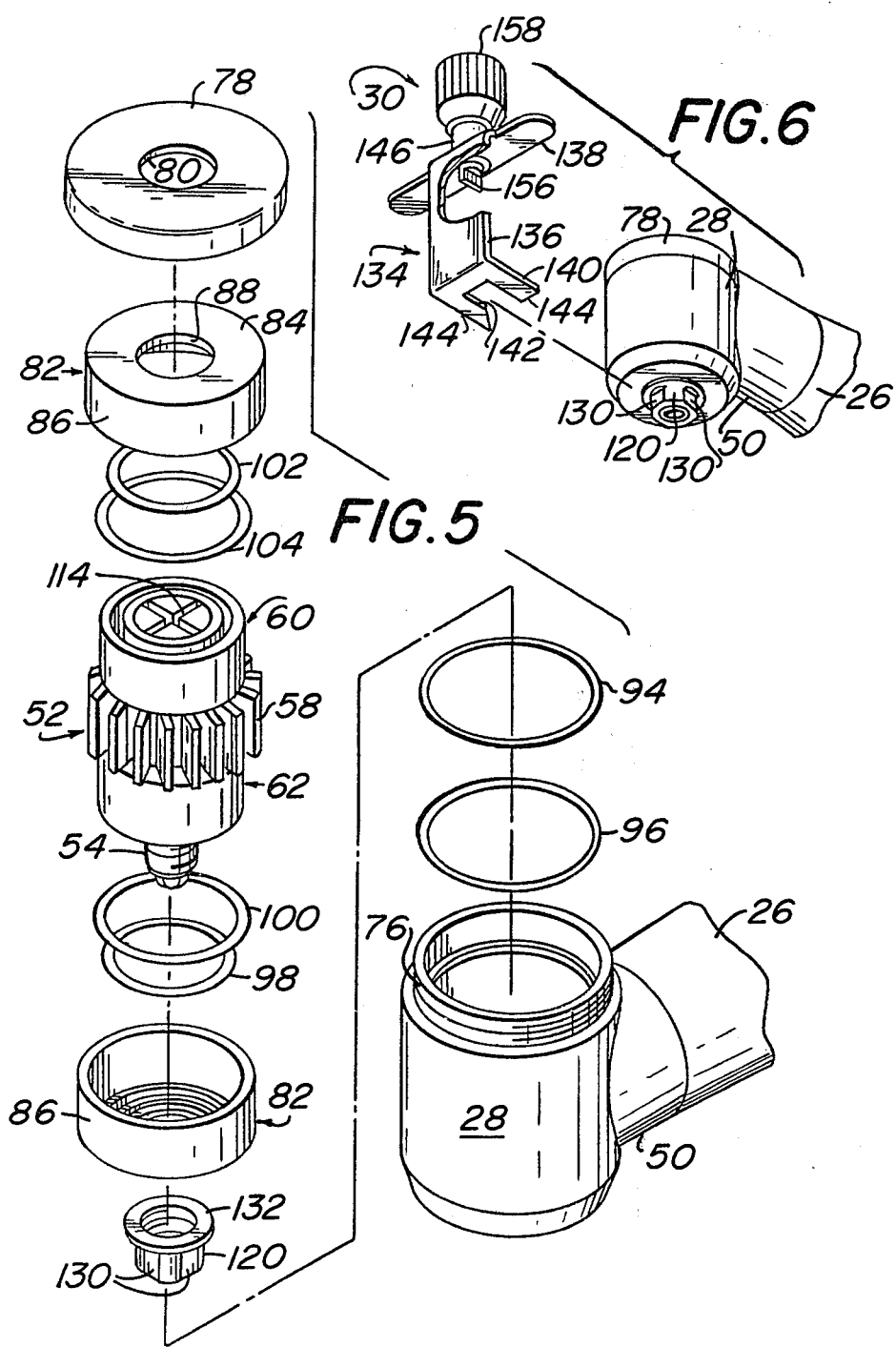

HANDPIECE

This invention relates to a dental handpiece, and more particularly, to a novel air driven dental handpiece that includes a novel mounting for the air turbine and a novel water spray system.

It is now a common practice in the dental art to supply rotative power to a dental handpiece through the use of an air driven rotor or turbine. Extremely high speeds have been attained utilizing pneumatically driven dental handpieces. One of the problems that has arisen with such handpieces is excessive bearing wear. Thus, the air driven turbines are generally mounted in ball bearings and the wear on the ball bearings has been found to be excessive. Usually, the ball bearings must be replaced in less than one year of use.

In one aspect of this invention, a resilient mounting is provided for the ball bearings, and the air turbine mounted therein. It has been found that this resilient mounting substantially increases bearing life. Additionally, it aids in absorbing vibration caused by the rotating bur when it contacts a tooth, thereby aiding the dentist in using the handpiece. It also deadens the sound of the rotating turbine, which is beneficial to both the patient and the dentist. Having the resilient mounting eliminates the need for precision balancing of the turbine, and further eliminates the need for pre-loading the bearings, as has been done in the past. The resilient mounting means of this invention is structurally different from that shown in U.S. Pat. No. 3,499,223.

In another aspect of this invention, the air and water mixture used to cool the rotating bur is formed at the point of egress from the handpiece. It is a common practice to mix the air and water externally of the handpiece for cooling the dental bur. Structure for accomplishing this result is shown in U.S. Pat. Nos. 3,199,196 and 3,499,223. In both of these prior patents, the air and water are mixed externally of the handpiece, and where the air and water tubes are adjacent each other, the spray produced from the mixture of the two results in large droplets of water. When utilizing the internal mixing of the instant invention, rather than producing large droplets of water, a very fine mist or fog is produced. The smaller droplets of water produced in the fog tend to remove more heat than is removed by the larger droplets of water. Although U.S. Pat. No. 3,199,196 does disclose internal mixing of water and air, this is in conjunction with a spray device surrounding the dental bur, which spray device is external of the handpiece. Accordingly, the external spray device can interfere with the dental bur when the handpiece is used in drilling a tooth. The device of this invention is totally confined within the handpiece, and will not present any interference with the rotating dental bur.

There is also disclosed in this application a novel chucking arrangement for the dental bur, and a chuck wrench used therewith. This aspect of the disclosure is covered in co-pending application Ser. No. 147,696, filed May 7, 1980, and entitled "DENTAL HANDPIECE AND COLLET WRENCH THEREFOR".

It is accordingly an object of this invention to provide a novel dental handpiece.

It is another object of this invention to provide a dental handpiece having a resiliently mounted turbine cartridge with ball bearings.

It is a further object of this invention to provide a dental handpiece having a novel water spray system.

These and other objects of this invention are accomplished by providing a dental handpiece comprising a tubular housing, a turbine housing at one end of said tubular housing, a turbine rotatably mounted within said turbine housing, bearing means associated with said turbine, said bearing means being resiliently mounted within said turbine housing, and means for securing a dental bur within said turbine.

Other objects and many of the attendant advantages of this invention will be readily appreciated as the same becomes better understood by reference to the following detailed description when considered in connection with the accompanying drawings wherein:

FIG. 2 is a partial sectional view of the handpiece of FIG. 1;

FIG. 3 is an end elevational view taken in the direction of line 3—3 of FIG. 1;

FIG. 4 is an enlarged sectional view taken along the line 4—4 of FIG. 2;

FIG. 5 is an exploded perspective view of the elements contained within the turbine housing of the handpiece of this invention;

FIG. 6 is a exploded perspective view of the wrench and turbine housing of the handpiece of this invention;

FIG. 8 is an enlarged sectional view taken along the line 8—8 of FIG. 7; and,

FIG. 9 is a side elevational view, partially in section, showing the mounting of the wrench on the handpiece of this invention.

Figure 1:
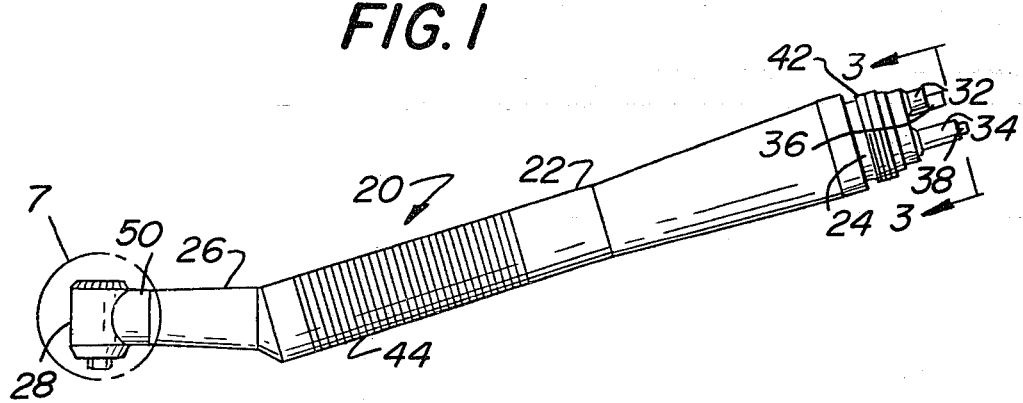
FIG. 1 is a side elevational view of the handpiece of this invention.

Referring now in greater detail to the various figures of the drawings wherein like reference characters refer to like parts, an air driven dental handpiece embodying the present invention is generally shown at 20 in FIG. 1. Device 20 basically comprises a hollow handle 22 and an adaptor block 24 at the rear end thereof. Handle 22 includes an angled neck 26 at the front end thereof, and a turbine housing 28 is mounted on neck 26. A wrench used in connection with the chucking mechanism of the turbine is generally shown at 30 in FIG. 6, and will be described in further detail hereinafter.

As best seen in FIG. 2, adaptor block 24 is secured in the end of hollow handle 22, as by a pressed fit. Passing through the adaptor block 24 is an air inlet tube 32 and an air exhaust tube 34. Tube 32 supplies the driving air for the turbine. A water tube 36 and an air tube 38 also pass through adaptor block 24. Water tube 36 provides coolant water for the bur and air tube 38 serves the dual function of aspirating the water and serving as a chip blower. Suitable controls, well known to the art, regulate the use of the air passing through tube 38 for either function. A rubber or plastic cushion 40 surrounds all the tubes passing through the adaptor block 24.

External connections are made with the various tubes passing through adaptor block 24 through the use of an adaptor nut, which is well known to the art. The adaptor nut is secured on the adaptor block 24 through threads 42 on the adaptor block. The adaptor nut provides gasketed connections with tubes 32, 34, 36 and 38 to provide incoming air and water. If desired, exhaust tube 34 can be exhausted to the atmosphere through the adaptor nut. The connection of the adaptor nut on the adaptor block is well known to the art, and is not illustrated herein.

Handle 22 is provided with a plurality of spaced, annular grooves 44 in the surface thereof. These grooves aid in the grasping of the handle 22, in a manner well known to the art. Water tube 36 is connected to a smaller diameter tube 46 within adaptor block 24. Similarly, air tube 38 is connected to a smaller diameter tube 48 within the adaptor block.

Figure 7:
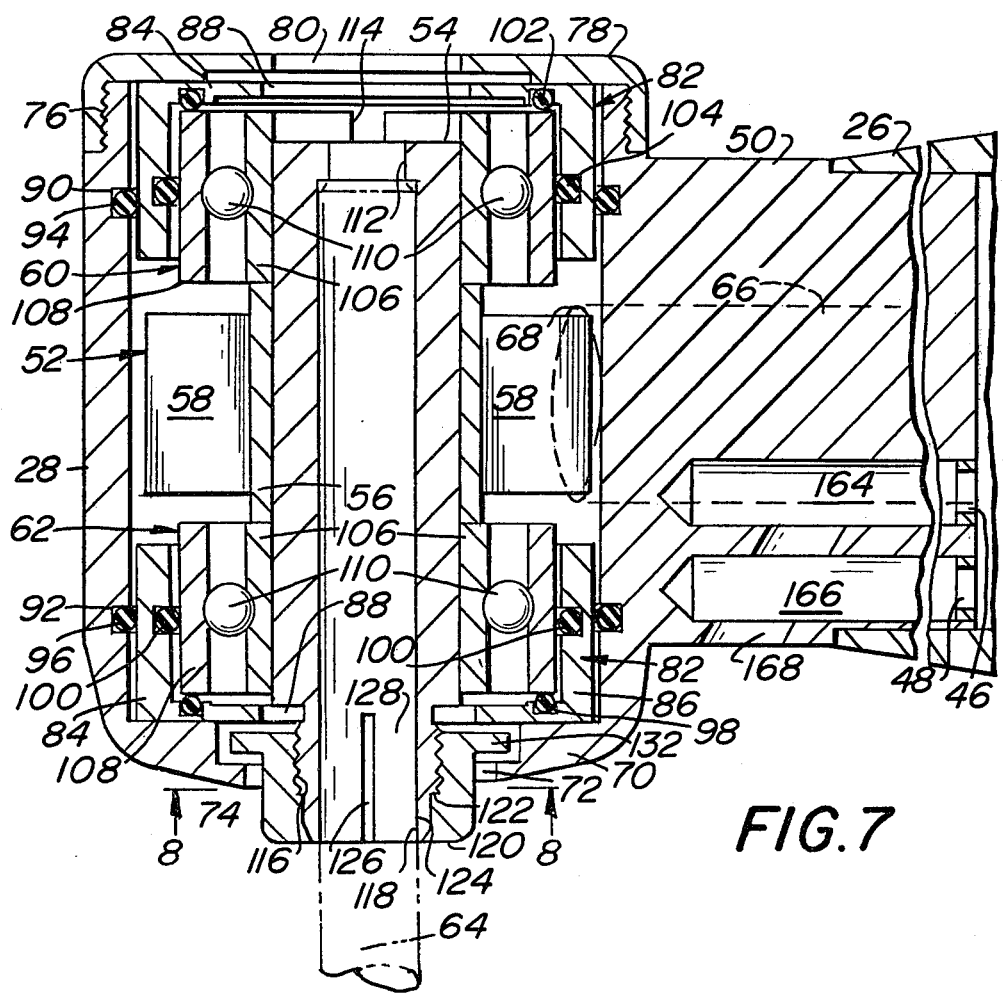
FIG. 7 is an enlarged sectional view taken in the area 7 of FIG. 1.

Referring to FIG. 7, it is seen that turbine housing 28 includes an extension 50. Extension 50 is received within neck 26, and secured therein, as by a pressed fit or welding. Mounted within turbine housing 28 is turbine cartridge 52. Turbine cartridge 52 comprises a collet 54, a rotor hub 56 secured thereon, rotor blades 58 integral with hub 56, upper ball bearing 60 and lower ball bearing 62.

In the operation of the handpiece, a dental bur 64 is secured in collet 54, in the manner described hereinafter. Air to drive the turbine is then furnished, via suitable controls, through tube 32 (FIG. 2). The tube 32 terminates in extension 50 of turbine housing 28 (FIG. 7), where it enters conduit 66 in the extension. Conduit 66 terminates in the wall of turbine housing 28 at opening 68. The impingement of the air exiting from opening 68 against rotor blades 58 causes the turbine to rotate within the turbine housing. Since the collet 54 is secured to the rotor hub, it will rotate therewith, thereby rotating the bur 64. Exhaust air passes through a second conduit (not shown) in extension 50, through the hollow handle 22, and exhausts through tube 34 (FIG. 2). The exhaust conduit is adjacent conduit 66, and has the same size as conduit 66.

To the extent described, the handpiece of this invention is basically the same in structure and function as the prior art handpieces. Thus, substantially all of the prior art handpieces rely on the same basic combination of elements to supply air to a turbine to obtain rotative power for a dental bur. The improvements of this invention relate to the mounting of the turbine cartridge and the supplying of coolant water to the rotating bur.

Turbine housing 28 is circular in interior cross-section, as best seen in FIG. 5. As seen in FIG. 7, the turbine housing includes a unitary bottom wall 70. A central opening 72 is formed in bottom wall 70. Wall 70 includes an annular interior recess 74. The upper end of turbine housing 28 is open, and includes exterior threads 76 (FIGS. 5 and 7) thereon. An end cap 78 is threadedly secured on turbine housing 28, and closes the same. As seen in FIG. 2, end cap 78 has surface grooves thereon to aid in securing the same in place. End cap 78 is provided with a central opening 80.

The elements mounted within turbine housing 28 in the assembled condition of the handpiece are best seen in FIG. 5. As seen therein, the turbine cartridge 52 comprising the collet, rotor and blades, and ball bearings is shown as a preassembled unit. A pair of isolator members 82 are provided. Each isolator member 82 includes a base disc 84 and a peripheral, unitary wall 86. Each disc 84 includes a central opening 88.

Referring to FIG. 7, it is seen that turbine housing 28 has an upper annular groove 90 and a lower annular groove 92 formed in the interior wall thereof. A rubber O-ring 94 is placed in upper groove 90 and rubber O-ring 96 is placed in lower groove 92. In assembling the handpiece, lower isolator 82 is first placed within turbine housing 28, and rests on bottom wall 70 of the housing. A rubber O-ring 98 is placed within a groove of the disc 84 of the lower isolator, and a rubber O-ring 100 is placed within a groove in the wall 86 of the lower isolator. With the lower isolator in place, the turbine cartridge 52 is then inserted into the turbine housing.

A rubber O-ring 102 is inserted in a groove in the disc 84 of upper isolator 82, and a rubber O-ring 104 is inserted in a wall 86 of the upper isolator 82. Thereafter, the upper isolator, with the O-rings in place, is placed on top of the upper ball bearing 60 (FIG. 7). Once the upper isolator has been inserted in place, the end cap 78 is screwed on the turbine housing 28, thereby completing the structure shown in FIG. 7.

As seen in FIG. 7, each of bearings 60 and 62 comprises an inner race 106, an outer race 108 and balls 110 positioned between the races. The inner races 106 are secured to collet 54 by a pressed fit, and accordingly rotate along with the collet and the rotor. The outer races 108 remain stationary during rotation.

It is thus seen that the isolators 82 and their associated rubber O-rings provide a total resilient mounting for the turbine cartridge. The isolators are resiliently mounted against the O-rings 94 and 96. The outer races 108 are resiliently mounted against the O-rings 98, 100, 102 and 104. It is this resilient mounting for the turbine cartridge that provides for the sound dampening, increased bearing life and vibration dampening of the handpiece of this invention.

Referring to FIG. 7, it is seen that collet 54 has an opening 112 at the top thereof. A crosscut is made in the top of collet 54 at opening 112, thereby forming slots 114 (see also FIG. 5). The bottom of collet 54 is externally threaded, as seen at 116 in FIG. 7. Below threads 116, the exterior wall of collet 54 is tapered inwardly, as shown at 118.

A collet nut 120 is threadedly secured on collet 54. The rotation of the collet relative to the collet nut raises and lowers the nut on the collet. A rim 122 is formed on the collet nut which abuts a similar rim on the collet. This limits the upward movement of the nut relative to the collet. The interior surface of the collet nut is inwardly tapered, as shown at 124. The taper 124 is complementary with the taper 118 of the collet. Collet 54 has a hollow bore, and four equally-spaced slots 126 are formed therein, thereby forming jaws 128 (see also FIG. 8).

Collet nut 120 has four equally spaced flattened surfaces 130 on the exterior surface thereof (see FIGS. 5 and 8). Collet nut 120 further includes an annular flange 132 projecting from the top thereof (FIGS. 5 and 7). The flange 132 is received within recess 74 of bottom wall 70 of turbine housing 28.

The wrench 30 and its function are best seen in FIGS. 6 and 9. The wrench includes a bracket 134 comprising a vertical wall 136, a top wall 138 and a bottom wall 140. Bottom wall 140 includes a central slot 142, thereby forming a pair of jaws 144. A tube 146 (FIG. 9), having an annular groove adjacent the bottom thereof, is snapped into an opening in top wall 138 of bracket 134, thereby securing the tube in place. Tube 146 has an integral top wall 148 having a central opening 150 therein. A rod 152 passes through opening 150. Rod 152 has a hub 154 adjacent the bottom thereof. The bottom of rod 152 terminates in a flat blade 156 (FIGS. 6 and 9).

The top of rod 152 is secured in a knob 158, as by a pressed fit (FIG. 9). As seen in FIGS. 6 and 9, knob 158 has surface grooving to aid in grasping the same. A compression spring 160 is telescoped over rod 152, and has one end abutting the undersurface of top wall 148 of tube 146 and the other end abutting the top of hub 154.

The wrench 30 is used for inserting or removing the dental bur 64 from the handpiece. When it is desired to utilize the wrench, the knob 158 is first raised, thereby raising the rod 152. The movement of the knob is indicated by arrow 162 in FIG. 9. When the knob 158 is raised, spring 160 will be compressed, and blade 156 of rod 152 will be within the confines of tube 46. At this time, the bracket 134 can be slid over turbine housing 28. A pair of flattened faces 130 of collet nut 120 are received in slot 142 and between jaws 144 of bracket 134. This secures the collet nut 120 in place, and prevents any rotation of the same.

Once the collet nut has been secured in place, knob 158 is released, thereby expanding spring 160. The knob 158 is rotated until blade 156 is received in a pair of aligned slots 114 (FIG. 5) in the top of the collet. The position of the blade 156 in the slots is shown in FIG. 9. Once the blade is in place, knob 158 is rotated. If the knob 158 is rotated in a counterclockwise direction, as viewed in FIG. 9, the collet nut 120 will be lowered relative to collet 54. Thus, since the collet is threadedly secured to the collet nut, as seen in FIG. 7, the rotating of the collet relative to the nut in a counterclockwise direction will tend to unthread the nut relative to the collet. When this is done, the pressure of tapered wall 124 of the collet nut against the tapered wall 118 of the collet will be removed, since these tapered walls will be separated. This permits the expansion of the jaws 128 of the collet about slots 126 (FIG. 8).

Once the jaws have been expanded, the dental bur 64 can be removed from the collet. The insertion of the dental bur is carried out by following the same procedure with the collet wrench 30. Thus, once the dental bur 64 has been inserted in the collet and the wrench is in the position shown in FIG. 9, the knob 158 is rotated in a clockwise direction. This in turn will rotate the rod 152, thereby rotating the collet 54 in which the blade 156 is engaged. When rotating in this direction, the collet nut 120 will be threadedly advanced relative to the collet 54, until the tapered wall 124 of the collet nut abuts the tapered wall 118 of the collet. Further advancement of the collet nut causes the jaws 128 of the collet to compress under the urging of the mating tapered walls. As the walls are compressed, the bur 64 will be held securely in place, it should be noted that the knob 158 and rod 152 are rotatable relative to tube 146 which is secured to bracket 134. The jaws 144 of the bracket prevent any rotation of the collet nut during the time that the collet is being rotated.

The threaded securement of the collet relative to the collet nut provides a positive grip on the dental bur, and insures concentric rotation of the dental bur during use of the handpiece. Utilizing the prior art resilient collets it has been found that the rotation of the dental bur can become non-concentric due to compression of the collet during the drilling of a tooth. This make drilling of the tooth more difficult, and can result in inaccurate or improper drilling.

One of the features of the collet and collet nut arrangement is the provision of the shoulder 122 on the collet nut and the adjacent shoulder on the collet. Thus, once the collet nut has been tightened to the position shown in FIG. 7, further tightening is prevented by the abutment of the two shoulders. This prevents the collapsing and breaking of the collet jaws if the dentist should inadvertently start to tighten the collet with no bur inserted therein.

Another feature of the collet nut is the provision of flange 132. If the dentist should inadvertently rotate the collet in a counterclockwise direction to too great an extent, it might be possible to totally remove the collet nut from the collet. If this should occur, the dentist might lose the collet nut, thereby rendering the handpiece unusable. However, having the flange 132 and further having the opening 72 of a smaller diameter then the diameter of the flange 132, if the dentist should inadvertently tend to overloosen the collet, the bottom wall of the flange 132 will contact the bottom wall 70 of the turbine housing 28, thereby preventing any further rotation of the collet. This will insure that the collet nut will never be removed from its threaded securement on the collet.

As an alternate embodiment, the opening 72 can be greater than the diameter of flange 132. In this case, the unthreading of the collet nut relative to the collet will be terminated when the flange 132 abuts the upper surface of the bottom wall 140 of bracket 134. In this case, the bottom wall of the bracket will prevent any further rotation of the collet.

It should be noted that during the rotation of the collet, all of the movable elements within the turbine housing will also rotate. Thus, the rotor and the inner races of the ball bearings will also rotate. The collet will remain at its fixed position within the handpiece, and the only movement will be that of the collet nut in a vertical direction. Thus, even though it is the collet that is being rotated, only the nut will move. The jaws 144 of the bracket 134 prevent the collet nut from rotating during the rotation of the collet, but the slot 142 is sufficiently wide to permit the collet nut to move vertically therein when the collet is being rotated.

The collet wrench and its function in connection with the collet have been described in detail herein solely for the purpose of completeness. It should be understood that the collet, collet nut and collet wrench are the subject of a separate invention, which is covered by aforementioned application Ser. No. 147,696.

Another feature of the handpiece is the coolant spray system. It has been found that the use of the high speed air driven dental handpieces has created a problem, namely, the generation of large amounts of frictional heat in a tooth that is being drilled. It has therefore become necessary to cool the tooth during the drilling thereof. The method of cooling which is almost exclusively used is that of directly supplying a water spray against the tooth while the drilling is being carried out.

Various spray devices have been developed for directing water against the tooth being drilled. Some of these spray devices are disclosed in U.S. Pat. Nos. 3,120,706, 3,199,196, 3,499,223 and 4,015,489. In most of these patents, and in the devices currently in use, the mixing of the air and water to provide a coolant spray takes place externally of the handpiece. Generally, the water and air are supplied from separate tubes, and are mixed after exiting from these tubes. Although U.S. Pat. No. 3,199,196 does disclose the mixing of air and water prior to the mixtures exiting the spray tubes, in this patent the spray is generated in an external device surrounding the dental bur. In the handpiece of this application, all mixing of the air and water occurs internally within the handpiece. Having the internal mixing prevents any interference by external spray tubes adjacent the dental bur. Furthermore, the external spray tubes can interfere with the dentist's viewing the tooth that is being drilled.

Referring now to FIG. 2, it is seen that the incoming coolant water enters the handpiece through tube 36 and passes through tube 46. As seen in FIG. 7, tube 46 terminates in extension 50 and enters bore 164 in the extension. Similarly, the coolant air to be mixed with the water enters the handpiece through tube 38 and passes through tube 48 within the handpiece. As seen in FIG. 7, tube 48 terminates in extension 50, and the air enters bore 166 in the extension. Bore 164 is in fluid communication with bore 166 via bore 168, which passes through bore 166 and into bore 164. Bore 168 is also in fluid communication with the exterior of the handpiece.

During the operation of the handpiece 20, air for driving the turbine enters the handpiece through tube 32, and drives the turbine in the manner described above. At the same time the air is admitted through tube 32, water is admitted through tube 36 and the coolant air enters through tube 38. The water ultimately enters bore 164 (FIG. 7) and exits from the bore 164 into bore 168. At this point, the water mixes with the air which is entering bore 166. The air aspirates the water, and the mixture of air and water exits from the handpiece through the bottom of bore 168. In view of the fact that the bore 168 is angled toward the bur 64, the air and water mixture will completely surround the bur and the area of the tooth that is being drilled.

In the prior art external spray systems, wherein the air and water are supplied by separate tubes, and are not mixed until they exit their respective tubes, the water is dispersed against the tooth in relatively large droplets. The premixing of the air and the water in the handpiece of this invention creates a very fine mist or fog of coolant water. The water droplets are substantially smaller than those produced by the external mixing. Having the finer mist aids in cooling the tooth that is being drilled, and more cooling is accomplished by having the finer mist than by having the relatively large droplets produced by the prior at spray devices. Additionally, since the cooling mist is produced internally of the handpiece, there is no interference with the drilling operation caused by the prior art external spray devices.

Without further elaboration, the foregoing will so fully illustrate our invention, that others may, by applying current or future knowledge, readily adapt the same for use under various conditions of service.

What is claimed as the invention is:

1. A dental handpiece comprising a tubular housing, a turbine housing mounted at one end of said tubular housing, a turbine rotatably mounted within said turbine housing, bearing means associated with said turbine, said bearing means comprising a pair of spaced ball bearings, said ball bearings having inner and outer races, said outer races being stationary and said inner races being adapted to rotated with said turbine, means to isolate each of said outer races from said turbine housing, means for resiliently mounting said outer races in said isolator means, means for resiliently mounting said isolator means in said turbine housing, and means for securing a dental bur within said turbine.

2. The dental handpiece of claim 1 wherein the means for resiliently mounting the outer races in said isolator means comprises at least one O-ring positioned between each isolator means and its associated outer race.

3. The dental handpiece of claim 2 wherein a pair of O-rings contact each outer race, with one of each pair contacting the outer race on the side thereof and the other of each pair contacting the outer race on the end thereof.

4. The dental handpiece of claim 3 wherein each O-ring is received within a recess in its associated isolator means.

5. The dental handpiece of claim 1 wherein the means for resiliently mounting said isolator means in said turbine housing comprises an O-ring positioned between each isolator means and said turbine housing.

6. The dental handpiece of claim 5 wherein the inner wall of said turbine housing includes recesses therein, with each O-ring positioned between the turbine housing and the isolator means being received in one of said recesses.

7. The dental handpiece of claim 1, and further including means within said tubular housing for furnishing a water spray on said dental bur.

8. The dental handpiece of claim 7 wherein said means for furnishing said water spray comprises an air tube within said tubular housing, a water tube within said tubular housing, said air tube terminating in a first bore in the end of said handpiece adjacent said turbine housing, said water tube terminating in a second bore in the end of said handpiece adjacent said turbine housing, and a third bore placing said first and second bores in fluid communication with each other, said third bore being in fluid communication with the exterior of said handpiece, and terminating on the exterior surface of said handpiece, whereby air and water entering their respective bores will mix and exit through said third bore, thereby projecting a water spray in the area of said dental bur.

9. A dental handpiece comprising a tubular housing, a turbine housing at one end of said tubular housing, a turbine rotatably mounted within said turbine housing, tube means adapted to furnish air to rotate said turbine, means for securing a dental bur within said turbine, and means within said tubular housing for furnishing a water spray on said dental bur, said means for furnishing said water spray comprising an air tube within said tubular housing, a water tube within said tubular housing, said air tube terminating in a first bore in the end of said handpiece adjacent said turbine housing, said water tube terminating in a second bore at the end of said handpiece adjacent said turbine housing, and a third bore placing said first and second bores in fluid communication with each other, said third bore being in fluid communication with the exterior of said handpiece, and terminating on the exterior surface of said handpiece, whereby air and water entering their respective bores will mix and exit through said third bore, thereby projecting a water spray in the area of said dental bur.

10. The dental handpiece of claim 9 wherein said third bore is angled in the direction of said dental bur.

11. The dental handpiece of claim 10 wherein said second bore is positioned above said first bore, whereby water will leave said second bore, pass into said third bore and mix with air at the intersection of said third and first bores prior to exiting from said third bore.

* * * * *